United States Patent [19]

Higashiyama et al.

[11] 4,038,270

[45] July 26, 1977

[54] MENTHOL GLYCOSIDE, PROCESS FOR PREPARING THE SAME AND METHOD FOR RELEASING MENTHOL THEREFROM

[75] Inventors: Tatsuo Higashiyama; Isao Sakata, both of Kasaoka, Japan

[73] Assignee: Toyo Hakka Kobyo Kabushiki Kaisha, Japan

[21] Appl. No.: 584,855

[22] Filed: June 9, 1975

Related U.S. Application Data

[63] Continuation of Ser. No. 273,455, July 20, 1972, abandoned.

[30] Foreign Application Priority Data

Aug. 27, 1971 Japan .................................. 46-065616
Aug. 27, 1971 Japan .................................. 46-065617

[51] Int. Cl.$^2$ ........................................... C07H 15/20
[52] U.S. Cl. ........................................ 536/4; 424/180; 426/534; 536/110
[58] Field of Search ........................ 260/210 R; 536/4

[56] References Cited

U.S. PATENT DOCUMENTS

| | | | |
|---|---|---|---|
| 2,049,758 | 8/1936 | Bertsch et al. | 536/4 |
| 2,218,569 | 10/1940 | White | 260/210 R |
| 2,235,783 | 3/1941 | White | 260/210 R |
| 3,152,115 | 10/1964 | Morel et al. | 260/210 R |
| 3,219,656 | 11/1965 | Boettner | 536/4 |
| 3,707,535 | 12/1972 | Lew | 260/210 R |

*Primary Examiner*—Johnnie R. Brown
*Attorney, Agent, or Firm*—William J. Daniel

[57] ABSTRACT

Water-soluble menthol glycosides are prepared by condensing menthol with a mono- or oligosaccharide, preferably a mono- or di-saccharide, i.e., a sugar, or acyl derivative thereof, using a condensing agent or catalyst as needed. These glycosides are hydrolyzed by carbohydrase enzymes, as occur in the human mouth, or common acids, releasing menthol, and provide a more persistent flavor than menthol alone.

8 Claims, No Drawings

MENTHOL GLYCOSIDE, PROCESS FOR PREPARING THE SAME AND METHOD FOR RELEASING MENTHOL THEREFROM

This is a continuation of Ser. No. 273,455, filed July 20, 1972 and now abandoned.

SUMMARY OF INVENTION

This invention relates to a process for preparing menthol glycosides represented by the following general formula:

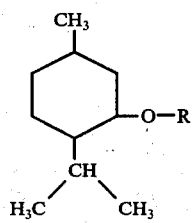

the products obtained by such process, and a method for releasing menthol from these products thereof. In the formula, R represents a residue of a mono- or oligosaccharide (hereinafter referred to simply as a saccharide).

BACKGROUND OF INVENTION

Menthols, for their inherent mint flavor and refreshing feeling, have been widely used for medicines, foodstuffs, liquids, tablets, creams and pastes for oral introduction, etc. Also, these compounds are known to possess minor pharmacological utility as an antipruritic, mild local anesthetic, and counterirritant, according to the Merck Index, 8th Edition. However, since menthols are only slightly soluble in water, their use has heretofore been limited to (a) mixing in the form of solid particles directly with the material to which the menthol is to be added, (b) making a suspension using an emulsifier, or (c) dissolving the menthol in an organic solvent such as alcohol, etc. Therefore, the use of menthols has been confined and thus a menthol substance having good solubility in water has been much desired.

However, though menthols in the free form have an inherent mint flavor and certain pharmacological activities as noted above, they lose this flavor and pharmacological activity when converted into derivatives by reaction with other compounds. For this reason, the synthesis of a water-soluble menthol compound has never been attempted or even conceived so far as known.

With an aim of developing a menthol compound having good solubility in water, extensive research has been carried out. As a result, it has been found and demonstrated for the first time that menthol glycosides have high solubility in water and, while they per se do not manifest the characteristic mint flavor of menthols, they release this mint flavor when they are resolved into menthol and sugar by hydrolysis with various carbohydrases or acids, etc., as indicated in the following chemical equation:

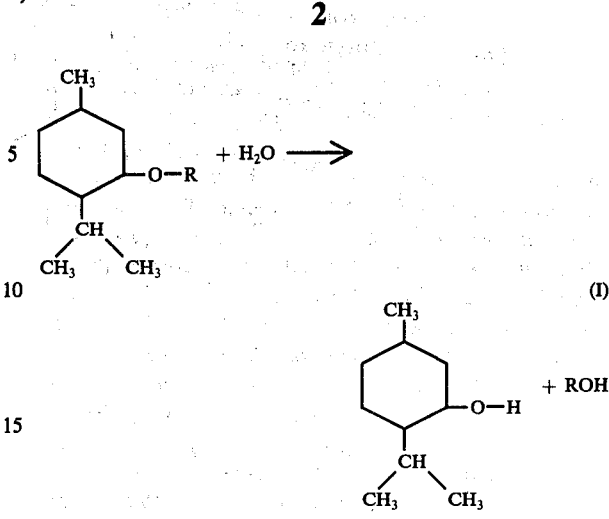

wherein R represents a residue of a monosaccharide or oligosaccharide. Thus, the menthol glycosides of this invention can be widely used as a water-soluble menthol substance.

It is well known that enzymes of the carbohydrase type are widely distributed in nature, occurring for example, in human saliva in the form of maltase, lactase, emulsin, amylase, etc., and that these enzymes are capable of hydrolyzing to cleave the glycosidic bond of glycosides. Further, it is also well known that common acids have a similar hydrolyzing capacity on glycosides in general.

It is conceived that a glycoside, in which the menthol acts as an aglycone, can manifest the mint flavor of the aglycone without drastic loss in water solubility, following the action of the enzyme or acid in cleaving the glucoside bond to yield the aglycone and sugar.

DETAILED DESCRIPTION OF PROCESS OF PREPARATION

According to the process of the invention, menthol glycosides are prepared by reacting a menthol with a monosaccharide or oligosaccharide (hereinafter referred to simply as saccharide) by the reaction shown in the following chemical equation:

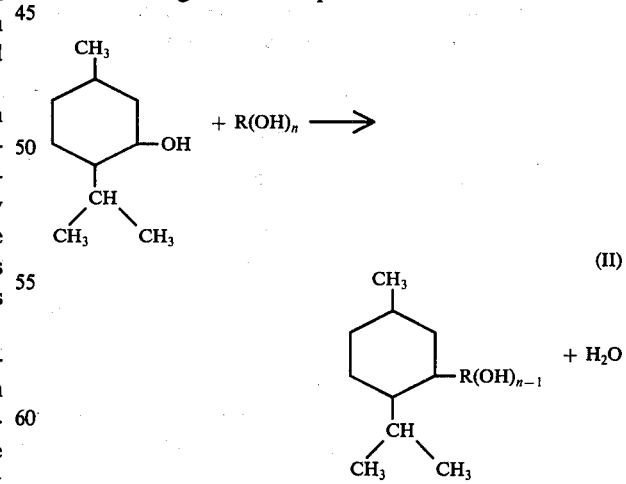

wherein R represents the saccharide residue and $n$ the number of hydroxyl groups thereon and at least 3.

In practicing the process of the present invention, it may be preferable to dissolve both of the reactants in a suitable solvent, for example, DMSO, etc., heat the resultant solution and, if necessary, add a catalyst or condensing agent thereto, but these are not the essential conditions. The reaction may proceed at room temperature, but it can be accelerated by an appropriate heating, for example, a heating on a water bath for an hour.

In principle, any saccharide capable of entering into the above reaction (II) and conferring the desired properties upon the ultimate glycoside, e.g., water-solubility, etc., will be satisfactory for the purposes of this invention. In particular, any of the mono-, di- or oligosaccharides referred to as sugars are preferred because of their unquestioned acceptance for human ingestion, even in large amounts, and readily water-solubility. These include glucose, mannose, galactose, laevulose, fructose, lactose, maltose, sucrose, and raffinose, to mention only the more commonly known members of this group. Polysaccharides such as starch, cellulose and the like are, in general, not contemplated here since they lack the desired water-solubility and the term oligosaccharide is used in its accepted sense of comprehending compounds containing several monosaccharide residues in the order of less than 10 but excluding polysaccharides containing hundreds or thousands of such residues.

The proportions of the reactants are not critical. The reaction schemes given herein indicate generally equimolar ratios are effective but smaller amounts of menthol give a useful yield and larger amounts are not precluded since any excess remains in the reaction medium.

The process of the present invention can also be practiced, yielding a preferable result, by first preparing an acyl derivative of the saccharide in order to prevent the decomposition of the saccharide during the course of the reaction and facilitate eventual crystallization, the resultant carboxylic ester derivative of the saccharide is then reacted with a menthol as before. The thus produced acylglycosides of menthol can then be subjected to hydrolysis under conditions preferentially attacking the ester linkage, i.e., in an alkaline aqueous medium with heating if needed, to separate the acyl moiety and produce the glycoside. This reaction mechanism is represented by the following chemical equations:

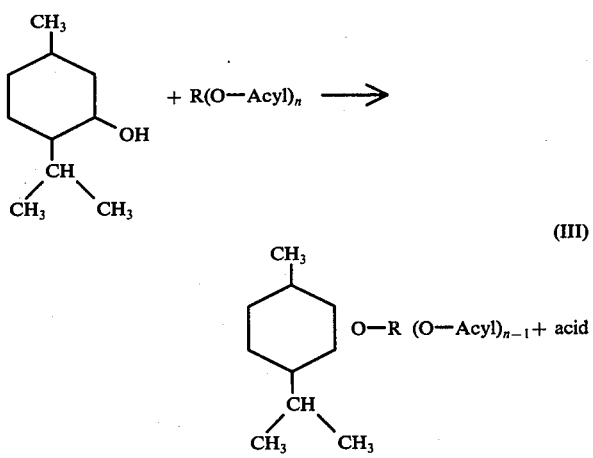

wherein Acyl represents an acyl group, R represents a residue of a saccharide, acid represents carboxylic acid and n represents an integer of at least 3.

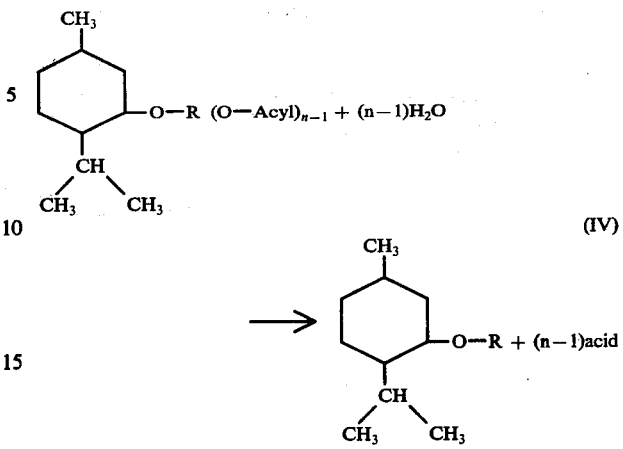

The acylated derivatives of saccharides include, as a matter of course, acylhalosaccharides, which give a preferable result. However, the acylated derivatives of saccharides are not limited to such compounds and any compounds may be included therein so long as they are acylated derivatives of saccharides.

Reaction III above using an acylhalosaccharide proceeds as follows:

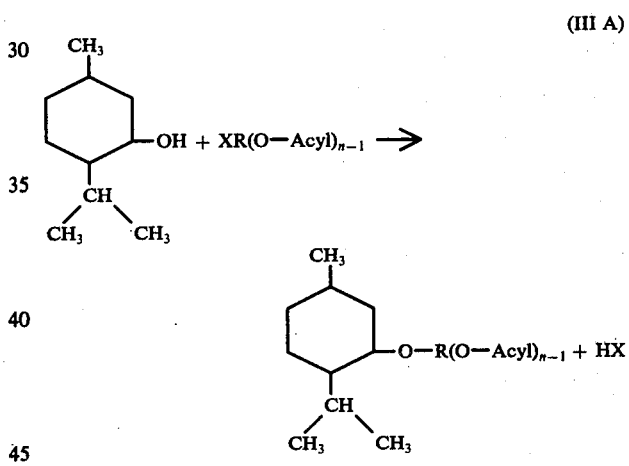

wherein X represents a halogen atom and the other symbols have the same significance as before.

Further, the addition of a suitable catalyst, the provision of a suitable solvent reaction medium, and heating may be preferable though they are not essential conditions.

The term "menthols" in the present invention means l-menthol and dl-menthol including isomers thereof. $H_2SO_4$, $H_3PO_4$, PPA, p-toluenesulfonic acid, etc., may be used as a catalyst, various carbonates, etc., as a condensing agent and DMSO, DMF, benzene, toluene, etc., as a solvent. Further, $Ag_2CO_3$ and the like may be employed, if necessary, to eliminate the halogen. These are, of course, mentioned only for illustration but not for limitation.

METHOD FOR RELEASING FREE MENTHOL

The rate of hydrolysis of the menthol glycosides of the invention with a carbohydrase-type enzyme or an acid varies depending upon the kind and quantity of the particular environment. For example, where l-menthyl-glucoside is held in the human mouth, it manifests its mint flavor quickly and the effect lasts far longer than that of l-menthol per se. Accordingly, it is evident that a gargling solution, for instance, containing the menthol glycoside is exceedingly useful as a practical working of the present invention.

If virtually instantaneous release of the free menthol is desired, this may be achieved, without depending upon the enzymes present in human saliva, by mixing an enzyme, etc., with the menthol glycoside in such a way that the reaction does not occur, or by keeping them separated and mixing them at the time of use. To increase the enzymatic activity, an enzyme activator may be added to give an optimum combination. Obviously, the carbohydrase enzyme employed in the process of the present invention may be any enzyme capable of cleaving the glycosidic bond of a menthol glycoside by hydrolysis, and the present invention is not limited to the use of the enzymes directly present in human beings and other living bodies. Also as regards the acid, any inorganic or organic acid that has the above-mentioned ability can be used in a wide range provided they are harmless to the human body under the specific conditions of use.

As mentioned earlier, since menthols and saccharides used as raw materials are inexpensive and widely available and the chemical operations involved in the invention are simple, the present invention is very advantageous from an economical point of view.

The menthol glycosides, when used, are resolved into menthol and sugar to release the mint flavor. Both menthol and sugar being in wide usage in many products intended for human application and/or consumption, the present menthol glycosides are very useful compounds having almost unlimited use as a water-soluble menthol for oral and topical administration, foodstuffs, pastes, lozenges, solutions, etc., for oral introduction and the like.

SPECIFIC EXAMPLES

The present invention is further explained by the details of the following examples.

EXAMPLE 1

A mixture of 5 g of l-menthol and 7 g of glucose is dissolved in 10 ml of DMSO with heating over a water bath and reacted with stirring. A solvent extraction is made by adding chloroform to the reaction mixture. Removing the solvent in a conventional manner, a highly viscous material is obtained, which is recrystallized from water, etc., to give 0.4 g of l-menthylglucoside. The yield of theory is 4%.

The thus obtained new substance has an m.p. of 73°–75° C and an optical rotation of $[\alpha]_D^{28} - 91.47°$ (C, 1.957 CHCl$_3$) and an elementary analysis as $C_{16}H_{30}O_6$(M$_w$318.4) reveals:

|  | c% | H% |
|---|---|---|
| Calculated | 60.35 | 9.50 |
| Found | 60.18 | 9.64 |

EXAMPLE 2

A mixture of 30 g of l-menthol and 10 g of glucose is made into a suspension with heating as before. To the suspension is added 10 g of H+-form of Amberlite (a trade name) IR-120 resin with stirring and the reaction is carried out for about 25 hours. The extraction and recrystallization is carried out in the same manner as in Example 1. As a result, 0.8 g of l-menthyl glucoside is obtained. The yield is 1.5%.

EXAMPLE 3

A mixture of 5 g of l-menthol and 10 g of acetylglucose is made into a solution with heating as before. The reaction is effected while adding a few drops of conc. H$_2$SO$_4$ with stirring. The reaction mixture is subjected to solvent extraction with ether and the solvent is removed in a conventional manner, leaving a highly viscous residue. This material is recrystallized from ethanol to obtain 3 g of l-menthyl acetylglucoside [m.p.: 130° C, $[\alpha]_D^{17} - 53.69°$ (C, 1.016 CHCl$_3$)]. The yield is 20%. Elementary analysis as $C_{24}H_{38}O_{10}$(M$_w$486):

|  | c% | H% |
|---|---|---|
| Calculated | 59.24 | 7.87 |
| Found | 59.23 | 8.01 |

Hydrolysis of the product with weak alkali in a conventional manner and crystallization gives 1.95 g of l-menthylglucoside. The yield is 98%.

EXAMPLE 4

A mixture of 5 g of neomenthol and 10 g acetylglucose is dissolved in 10 ml of benzene and reacted while adding a few drops of PPA with stirring and heating as before. The reaction mixture is treated in the same manner as in Example 3 to obtain 6.7 g of neomenthyl acetylglucoside [m.p.: 136.5° – 137.5° C, $[\alpha]_D^{20} + 1.85°$ (C, 0.918 CHCl$_3$)] and finally 4.35 g of neomenthyl glucoside. The yield is 44%.

EXAMPLE 5

10 g of l-menthol and 20 g of acetobromoglucose are mixed and made into a solution with heating. To the solution is added 5 g of dry silver carbonate. The reaction is carried out for one hour with stirring in a reactor equipped with a cooler fitted a calcium chloride tube. The reaction product is subjected to solvent extraction with ether and the extract is subjected to filtration thereby silver bromide is recovered. The solvent is removed from the filtrate in a conventional manner to obtain a viscous material. This material is treated in the same manner as in Example 3 to obtain 15 g of l-menthyl acetylglucoside and finally 9.75 g of l-menthyl glucoside. The yield is 49%.

EXAMPLE 6

10 g of neomenthol and 20 g of acetylbromoglucose are mixed and treated in the same manner as in Example 5 to produce 15 g of neomenthylacetylglucoside. Neomenthylglucoside can be obtained therefrom in the same way as in Example 5.

EXAMPLE 7

10 g of dl-menthol and 20 g of acetobromoglucose are mixed and treated in the same manner as in Example 5 to produce 15 g of -dl-menthylacetylglucoside (m.p.: 165°–168° C $[\alpha]_D \pm 0°$). dl-menthylglucoside can be obtained therefrom in the same way as in Example 5.

EXAMPLE 8

5 g of l-menthol and 10 g of acetobromogalactose are mixed and treated in the same manner as in Example 5 to result in 6 g of l-menthylacetylgalactoside [m.p.:

117°–118° C [α]$_D^{30}$ + 23.55° (C, 4.990 CHCl$_3$)]. The yield is 40%. l-menthylgalactoside can be obtained therefrom in the same way as in Example 5.

EXAMPLE 9

5 g of l-menthol and 10 g of acetobromosucrose are mixed and treated in the same manner as in Example 5 to produce 3 g of l-menthylacetylglucose. The yield is 20%. l-menthylglucose can be obtained therefrom in the same way as in Example 5.

EXAMPLE 10

10 mg of l-menthyl glucoside is dissolved in 1 ml of water. To the solution is added 1 ml of acetic acid buffer solution (pH: 5.25, 0.05M) and then 1 ml of β-glucosidase solution (emulsion) (20 mg in 1 ml). Further, to this mixture is added water to make up a total volume of 5 ml. The reaction is carried out at 36°–37° C with stirring. The occurrence of a hydrolyzing reaction can be confirmed by a thin layer chromatography and such tests reveal that the hydrolysis is virtually complete after one minute. A quantitative analysis of the liberated l-menthol determined by gas chromatography reveals 4.7 mg (calculated: 4.9 mg).

EXAMPLE 11

1 ml of a 1% menthyl glucoside solution is charged in a test tube and 0.5 ml of a 10% hydrochloric acid solution is added thereto. The test tube is corked tightly and heated on a boiling water bath for 15 minutes. The hydrolyzing reaction is confirmed in the same manner as in Example 10 and a quantitative analysis of the l-menthol reveals 4.6 mg (calculated: 4.9 mg).

EXAMPLE 12

A 0.1% l-menthol solution is prepared by mixing 30 g of ethyl alcohol, 1.2 g of a surface active agent, 145.65 g of distilled water and 0.15 g of menthol. The mixed solution is diluted twice with distilled water to prepare a control solution. A separate test solution is prepared by dissolving 0.15 g of menthyl glucoside in 100 g of distilled water.

Sensory tests were conducted by oral administration using five persons selected at random. After rinsing the mouth with city water, each of the subjects held 5 ml of the test solution in the mouth for 5 minutes and then expectorated. The mint flavor was evaluated in such a manner as "not perceptible (−)," "perceptible (+)," "strongly perceptible (++)" and "very strongly perceptible (+++)" using the strong initial flavor of the control solution as the basis for comparison at the peak level. These evaluations were made at 5 second intervals for the first minute after expectoration, then at 1 minute intervals up to an elapsed time of 25 minutes. Similar evaluations were made of the control solution. The results of these observations appear in the following tabulation.

TABLE I
PERSISTENCE OF MINT FLAVOR OF MENTHOL GLYCOSIDE VS MENTHOL PER SE

| Subject | | 5 sec. | 10 | 15 | 20 | 25 | 30 | 35 | 40 | 45 | 50 | 55 |
|---|---|---|---|---|---|---|---|---|---|---|---|---|
| A | Test solution | − | − | + | + | + | + | + | + | + | + | ++ |
| | Control solution | +++ | +++ | +++ | ++ | ++ | + | + | + | + | + | + |
| B | Test solution | − | − | − | − | − | + | + | + | + | + | + |
| | Control solution | +++ | +++ | +++ | +++ | +++ | +++ | ++ | ++ | ++ | ++ | + |
| C | Test solution | − | − | − | − | − | + | + | + | + | + | ++ |
| | Control solution | +++ | +++ | +++ | +++ | +++ | ++ | ++ | ++ | ++ | + | + |
| D | Test solution | − | + | + | + | + | + | + | + | + | + | + |
| | Control solution | +++ | +++ | +++ | ++ | ++ | + | + | + | + | + | + |
| E | Test solution | − | − | − | − | − | + | + | + | + | + | + |
| | Control solution | +++ | +++ | ++ | ++ | ++ | ++ | + | + | + | + | + |

| Subject | | 1 min | 2 | 3 | 4 | 5 | 6 | 7 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|
| A | Test solution | ++ | ++ | +++ | ++ | ++ | ++ | + | + | + | + | − | − | − | − | − | − | − | − | − |
| | Control solution | + | + | + | − | − | − | − | − | − | − | − | − | − | − | − | − | − | − | − |
| B | Test solution | ++ | ++ | ++ | ++ | ++ | ++ | ++ | + | + | + | + | + | + | + | − | − | − | − | − |
| | Control solution | + | + | + | + | + | − | − | − | − | − | − | − | − | − | − | − | − | − | − |
| C | Test solution | ++ | ++ | +++ | ++ | ++ | ++ | ++ | + | + | − | − | − | − | − | − | − | − | − | − |
| | Control solution | + | + | + | + | − | − | − | − | − | − | − | − | − | − | − | − | − | − | − |
| D | Test solution | + | ++ | +++ | ++ | ++ | + | + | + | + | + | + | + | + | + | + | − | − | − | − |
| | Control solution | + | + | + | + | + | + | + | + | − | − | − | − | − | − | − | − | − | − | − |
| | Test | | | | | | | | | | | | | | | | | | | |

TABLE I-continued

| | | PERSISTENCE OF MINT FLAVOR OF MENTHOL GLYCOSIDE VS MENTHOL PER SE | | | | | | | | | | | | | | | | | | | |
|---|---|---|---|---|---|---|---|---|---|---|---|---|---|---|---|---|---|---|---|---|---|
| E | solution | + | + | ++ | +++ | ++ | ++ | + | + | + | + | + | + | + | + | + | + | + | + | + | − |
| | Control solution | + | + | + | + | + | + | + | + | + | + | − | − | − | − | − | − | − | − | − | − |

As the table reveals, the refreshing mint flavor given by the products of the present invention was as strong as that given by l-menthol itself. Moreover, the present product began to manifest the mint flavor at a slower rate, i.e., in 10 to 30 seconds, reaching a maximum effect in 3 to 4 minutes. The duration of the effect was much longer until about 20 minutes.

EXAMPLE 13

5 g of l-menthol and 10 g of acetobromolactose were mixed and treated in the same manner as in Example 5 to result in 2 g of l-menthylacetyllactoside [m.p.: 86°–87° C $[\alpha]_D^{27}$ − 3.82° (C, 5.099 CHCl$_3$)]. The yield is 8%. The procedure to obtain l-menthyllactoside therefrom was the same as that of Example 3.

In the foregoing disclosure, the abbreviations PPA, DMF and DMSO represent polyphosphoric acid, dimethylformamide and dimethylsulfoxide, respectively.

What is claimed is:

1. A substantially water-soluble menthol glycoside having the general formula:

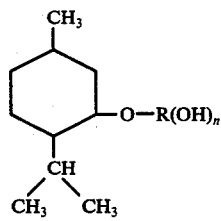

where R is the residue of lactose, maltose or raffinose and $n$ is the number of hydroxyl groups on said residue.

2. A method of preparing a substantially water-soluble menthol glycoside having the general formula:

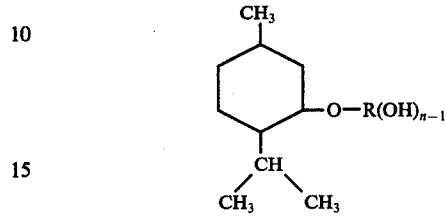

wherein:
R is the residue of a sugar and
$n$ is the number of hydroxyl groups,
comprising the steps of contacting menthol and a sugar or sugar ester having the formula:

wherein:
X is hydrogen or carboxylic acyl and
R and $n$ have the same significance as above, and
Z is a halogen atom or OX, in dimethyl sulfoxide, dimethyl formamide, benzene, or toluene as a reaction medium at a temperature from about room temperature up to about 100° C in the presence of an acidic condensation catalyst or a condensing agent, recovering the resultant product, and where X is carboxylic acyl hydrolyzing the product with alkali to produce the free glycoside.

3. The method of claim 2 wherein said condensation is carried out with mild heating up to about 100° C.

4. The method of claim 2 where said menthol and said sugar are contacted in generally equi-molar ratios.

5. The method of claim 2 wherein said carboxylic acyl is lower carboxylic acyl.

6. The method of claim 2 wherein X is hydrogen or acetyl.

7. The method of claim 2 wherein said glucoside is recovered by extracting the reaction mixture with a volatile organic solvent, removing said solvent, and re-crystallizing the residue with a polar liquid.

8. The method of claim 2 wherein said menthol and sugar are contacted from about 1 to about 25 hours.

* * * * *